(12) United States Patent  (10) Patent No.: US 6,494,845 B2
Rutenberg  (45) Date of Patent: Dec. 17, 2002

(54) RETRACTABLE BRUSH FOR USE WITH ENDOSCOPE FOR BRUSH BIOPSY

(75) Inventor: Mark Rutenberg, Monsey, NY (US)

(73) Assignee: Oralscan Laboratories, Inc., Suffern, NY (US)

( * ) Notice: Subject to any disclaimer, the term of this patent is extended or adjusted under 35 U.S.C. 154(b) by 0 days.

(21) Appl. No.: 09/849,085

(22) Filed: May 4, 2001

(65) Prior Publication Data

US 2002/0165467 A1 Nov. 7, 2002

(51) Int. Cl.⁷ .............................................. A61B 10/00
(52) U.S. Cl. ............................. 600/569; 604/1; 606/161
(58) Field of Search ................................. 600/562, 569, 600/570, 572; 604/1; 606/161

(56) References Cited

U.S. PATENT DOCUMENTS

| | | | | |
|---|---|---|---|---|
| 2,955,591 A | * | 10/1960 | MacLean ............. | 128/DIG. 14 |
| 5,562,102 A | * | 10/1996 | Taylor ......................... | 128/751 |
| 5,578,018 A | * | 11/1996 | Rowland et al. ............ | 600/562 |
| 5,722,423 A | * | 3/1998 | Lind et al. .................. | 600/562 |
| 5,899,850 A | * | 5/1999 | Ouchi ......................... | 600/104 |
| 6,030,397 A | * | 2/2000 | Monetti et al. ............. | 606/159 |
| 6,066,102 A | * | 5/2000 | Townsend et al. .......... | 600/104 |
| 6,258,044 B1 | * | 7/2001 | Lonky et al. ............... | 600/562 |

* cited by examiner

*Primary Examiner*—Teresa Walberg
*Assistant Examiner*—Thor Campbell
(74) *Attorney, Agent, or Firm*—Levisohn, Lerner, Berger & Langsam, LLP

(57) ABSTRACT

A retractable brush structure is attached to a cylindrical rigid rod which in the closed position passes through a channel in an endoscope. After the closed brush passes through the endoscope, the brush is opened and moves transversely to the tissue in order to remove cells from an area under examination. The brush is closed and withdrawn from the endoscope and sample tissue is removed from said brush for examination after it is withdrawn from the endoscope.

13 Claims, 2 Drawing Sheets

RETRACTABLE BRUSH FOR USE WITH ENDOSCOPE FOR BRUSH BIOPSY

FIELD OF THE INVENTION

The present invention is directed to a method and apparatus for obtaining transepithelial specimens of body surfaces using a non-lacerating technique. Specifically, the invention is directed to retractable tools such as a brush, used with endoscopes, for sampling squamous epithelium from lesions found from the nose to the throat and in similar body tissues. The invention is also directed to an improved apparatus for non-lacerational testing of lesions that involve the epithelium of the nasopharynx, hypopharynx, pharynx, trachea, larynx, and the upper esophagus.

BACKGROUND OF THE INVENTION

Cancers of the oral cavity and pharynx are a major cause of death from cancer in the U.S., exceeding the U.S. death rates for cervical cancer, malignant melanoma and Hodgkin's disease. According to the American Cancer Society's Department of Epidemiology and Surveillance, an estimated 30,750 new cases of oral cancer were diagnosed in the U.S. during 1997, a figure which accounts for 2% to 4% of all cancers diagnosed annually.

Despite advances in surgery, radiation, and chemotherapy, the mortality rate of oral cancer has not improved in the last 20 years. Ultimately, 50% of patients die from their malignancy, and 8,440 U.S. deaths were predicted for 1997. There are several reasons for the high mortality rate from oral cancer, but undoubtedly, the most significant factor is delayed diagnosis. Studies have demonstrated that the survival and cure rate increase dramatically when oral cancer is detected at an early stage. For example, the 5-year survival rate for patients with localized disease approximates 79% compared to 19% for those with distant metastases. Unfortunately, approximately two thirds of patients at time of diagnosis have advanced disease, and over 50% display evidence of spread to regional lymph nodes and distant metastases.

Delay in the diagnosis of oral and pharynx cancer is often the result of the limited diagnostic tools available in the prior art. The dentist or physician who detects such a lesion which is not clearly suggestive of a precancer or cancer clinically, and who is limited to the prior art tools and methods, is faced with a quandary. Approximately 5–10% of adult patients seen in a typical dental practice exhibit some type of oral lesion, yet only a small proportion (approximately 0.5% to 1%) are precancerous or cancerous. These oral lesions are commonly evidenced as a white or reddish patch, ulceration, plaque or nodule in the oral cavity. The overwhelming majority of these lesions are relatively harmless; however, the multitude of poorly defined lesions in the oral cavity can be confounding to the clinician. A diverse group of oral lesions may be easily confused with malignancy, and conversely, malignancy may be mistaken for a benign lesion. Benign tumors, reactive processes, traumatic lesions, oral manifestations or systemic diseases, inflammatory oral disorders, and bacterial, viral and fungal infections all display similar oral features thereby impeding establishment of an accurate clinical diagnosis.

The only reliable means currently available in the prior art to determine if a suspect oral lesion is pre-cancerous or cancerous, is to incise or excise (i.e. lacerate) the lesion surgically with either a scalpel or a laser so that a histological section of the removed tissue can be prepared for microscopic evaluation. Histology can be generally defined as the microscopic inspection or other testing of a cross section of tissue. This prior art form of oral surgical biopsy is generally performed by a surgeon, and is often inconvenient, painful, and expensive.

Since the majority of oral abnormalities detected clinically prove benign when tested microscopically, and given the limitations of biopsy, including cost, inconvenience, pain and potential for complications, relatively few oral lesions are subjected to biopsy. It is primarily for this reason that only oral lesions with clinical features strongly suggestive of cancer or precancer are referred for biopsy as described in the prior art. As a result, many patients with ominous, but visually less suggestive lesions are allowed to progress to advanced oral cancer, with their condition undiagnosed and untreated.

The oral epithelium is substantially identical to the epithelium of the nasopharynx, hypopharynx, pharynx, trachea, larynx, and the upper esophagus. As a result, otolaryngology currently suffers from the effects of the same diagnostic dilemma which affects dentistry, i.e. the inability to clinically distinguish between common benign-appearing lesions and identically appearing pre-cancerous and early cancerous lesions. Thus, the only two cancers in the U.S. which have not improved in mortality in the last thirty years are oral cancer and laryngeal cancer.

In many environments including those identified above, endoscopes are used to examine interior parts of the body which are inaccessible to ordinary visual observation. Observation of these inner parts with an endoscope is for purposes of locating pathological areas, trying to identify them using the endoscopic visual instrument and determining how to diagnose and treat such visualized areas.

Potential abnormalities in various portions of the body may be apparent to a visual observer because of certain lesions appearing at the visualized tissue in the organ or area being observed.

Common, benign-appearing nose and throat lesions are usually noticed by the otolaryngologist during a routine, office examination of the throat which is typically conducted using a type of endoscope, known as a flexible nasopharyngoscope. This thin optical tube is easily threaded from the patent's nose into the throat and requires only a local anesthetic sprayed into the nose. This routine office procedure is performed by the average otolaryngologist many times each day.

The diagnostic dilemma for the otolaryngologist that is posed by the identical appearance of benign and pre-cancerous lesions is actually more acute than it is for the dentist. Although invasive and therefore avoided, a scalpel biopsy of the oral cavity is typically performed as an office procedure. Only local anesthetic is required, and bleeding from a scalpel biopsy of the oral cavity does not pose any aspiration danger. In contrast, a scalpel biopsy in many areas of the throat cannot be performed as an office procedure. This is because a scalpel biopsy in many areas of the throat may result in potentially dangerous aspiration of blood if the procedure is not performed under general anesthesia.

Referral of the patient for an operating room procedure requiring general anesthesia is both expensive and intrusive, and may expose the patient to other risks such as anesthesia and infection risk. The otolaryngologist is therefore hesitant to scalpel biopsy most benign-appearing throat lesions although they may represent the most treatable stage of a pre-cancer or cancer.

In many body sites, but not the oral cavity, a technique known as cytology is commonly utilized as an alternative to performing a lacerating biopsy and histological evaluation. In these body sites, pre-cancerous and cancerous cells or cell clusters tend to spontaneously exfoliate, or "slough off" from the surface of the epithelium. These cells or cell clusters are then collected and examined under the microscope for evidence of disease.

Since prior art cytology is directed towards the microscopic examination of spontaneously exfoliated cells, obtaining the cellular sample is generally a simple, non-invasive, and painless procedure. Exfoliated or shed cells can often be obtained directly from the body fluid which is contiguous with the epithelium. Urine can thus be examined for evidence of bladder cancer, and sputum for lung cancer. Alternatively, exfoliated or shed cells may be obtained by gently scraping or brushing the surface of a mucus membrane epithelium to remove the surrounding mucus using a spatula or soft brush. This is the basis for the well known procedure known as the Pap smear used to detect early stage cervical cancer.

Because of the ease by which a cellular sample can be obtained from these body sites, prior-art cytology is typically utilized to screen asymptomatic populations for the presence of early stage disease. In the cervical Pap smear, for example, the entire surface area of the cervical regions where cancer generally occurs is gently scraped or brushed to collect and test the mucus from those regions. Abrasion of the underlying cervical epithelium is undesired, as it can cause bleeding and discomfort to the patient. This procedure is thus typically performed when no particular part of the cervix appears diseased, and when no suspect lesion is visible.

The design of prior art cytology sampling instruments reflects their use to sweep up cells which were spontaneously exfoliated and present on the superficial epithelial surface. Since prior-art cytology brushes need only to gently remove surface material, they are designed of various soft materials which can collect the cervical mucous with minimal abrasion to the underlying epithelium. These cytology sampling instruments therefore either have soft bristles, soft flexible fimbriated or fringed ends, or even, as in the case of the cotton swab or spatula, no bristles at all.

Examples of prior art cytological sampling tools include the wooden, metal or plastic spatula. According to the traditional method of Pap smear sampling, the spatula is placed onto the surface of the cervix and lightly depressed or scraped across the surface of the cervix to pick up exfoliated cells.

Further examples of prior art cytological sampling tools include the Cytobrush®; a device which uses soft and tapered bristles to sample shed cells from the cervical canal. U.S. Pat. No. 4,759,376, which allegedly covers this product, likewise describes a conical tapered soft bristle brush (a mascara brush shape) which is placed into the cervical canal and rotated for endocervical sampling. U.S. Pat. No. 4,759,376 teaches that the bristles "are to be relatively soft such as that of a soft toothbrush to more readily bend and avoid damaging the tissues." By way of further example, physicians have long used the common swab, commercially known as the Q-Tip®, to perform endocervical sampling.

Other prior art cytological sampling tools designed to obtain a cytological sample from the cervix may combine both endocervical and exocervical sampling regions into one device. These devices swab the surface of mucous-covered tissue by soft brushing the mucous layer of the endocervix and exocervix at the same time, thereby collecting the cells contained in the mucous layer tissue of those surfaces. These devices include the Unimar®-Cervex Brush™, a brush that has a contoured flat comb-like head with a single layer of flexible plastic bristles (similar to a flat paint brush having only one row of bristles) in which the center bristles are longer than the bristles on the ends. According to the method of use for the device, the center bristles are inserted into the cervical canal until the lateral bristles bend against the exocervix. The device is then removed and the cells are swabbed across a microscope slide similar to painting with a paintbrush.

Similarly, the Bayne Pap Brush™, which Medical Dynamics, Inc. represents is covered by U.S. Pat. No. 4,762,133, contains a center arm, made of soft DuPont bristles, running horizontal to the cervical canal and a second arm of soft bristles at ninety degrees to the first arm, creating an L-shape. The center arm is placed within the cervical canal and then rotated. Upon rotation, the soft bristles of the second arm automatically sweep the surface of the exocervix in a circular motion thereby sampling the exocervix along with the endocervix.

Although cytology has been adopted for use in several other body sites, it has not been found useful to test questionable lesions of the oral areas. This is in large part due to the fact that the prior art devices and methods used to obtain a cellular sample for cytology are unsatisfactory when used to sample lesions of the oral and nasal areas and areas containing similar epithelia. Unlike the uterine cervix, questionable lesions of the oral cavity and similar epithelia may be typically coated with multiple layers of keratinized cells. This "keratin layer" forms a relatively hard "skin-like" coating over the surface of the lesion and may thus hide the abnormal cells lying underneath it and prevent their exfoliation from the surface.

As noted above, the design of prior art cytology sampling instruments reflect their use in tissues where spontaneously exfoliated abnormal cells are commonly present on the surface of an area of epithelium that harbors disease. These cytology sampling instruments therefore either have soft bristles, soft flexible fimbriated ends, or even no bristles at all. Since prior-art cytology brushes only need to gently remove surface material, they are designed of various soft materials which can collect the cervical mucous with minimal abrasion to the underlying epithelium.

While abnormal cells can spontaneously exfoliate to the epithelial surface and be gently removed by prior art instruments in the uterine cervix and other similar tissues, in many oral cavity lesions the abnormal cells never reach the surface because they are blocked by the keratin layer. This limitation is a major cause of the high false negative rate of prior art cytological testing to detect lesions of the oral cavity. That is, a large proportion of oral lesions found to be positive using lacerating biopsy and histology are found to be negative using cytology. In one major study, this false negative rate was found to be as high as 30%.

It is largely due to this lack of correlation between histology and prior art oral cytology that there is currently no significant use of oral cytology in the United States or elsewhere to test questionable oral lesions. Since it is well known that dangerous, truly cancerous oral lesions may commonly be reported as "negative" using prior art cytologic sampling techniques, prior art cytologic techniques offer little as a reliable diagnostic alternative to the lacerating biopsy and histology.

SUMMARY OF THE INVENTION

An object of the present invention to provide an apparatus and method for sampling epithelial cells from the anatomy without the pain or injury of lacerational biopsies.

Another object of this invention is to provide a brush biopsy device conveniently used with endoscopes so as to effectively sample tissue in a questionable area without needing a lacerational technique.

A further object of the present invention to provide an apparatus for sampling epithelial tissue in the nasopharynx, hypopharynx, pharynx, trachea, larynx, and the upper esophagus.

Still another object of this invention includes utilizing such a brush technique for use with endoscopic examination in any area in which sampling of questionable tissue through non-lacerational techniques provide an enhanced medical procedure as contrasted with current lacerational techniques employed.

It is a further object of the present invention to provide a non-lacerating apparatus which may readily sample cells from all levels of a surface epithelial lesion, including the basal, intermediate and superficial layers of the lesion.

Other objects and advantages and features this invention will become more apparent from the following description.

In accordance with the present invention, an apparatus is provided for sampling all types of epithelium, particularly squamous epithelium, from lesions found in the nasopharynx, hypopharynx, pharynx, trachea, larynx, and the upper esophagus. Further, in accordance with the invention, an improved method is provided for testing questionable lesions found in the epithelium of the nasopharynx, hypopharynx, pharynx, trachea, larynx, and the upper esophagus and other body tissues. The method invented involves exerting sufficient pressure in the lesion area with a surface or edge capable of dislodging cells in and under a keratinized layer.

For purposes of this patent application, the prior art scalpel procedure is defined as lacerational, whereas the novel invention herein is non-lacerational and therefore minimally invasive. To the extent that an abrasive brush has characteristics that may cause minor discomfort and/or bleeding, there is substantial difference between the prior art scalpel trauma and the minimal trauma associated with the present invention.

The above and other objects are accomplished by providing a channel in the longitude interior of an endoscope through which a retractable brush may pass. The brush is formed so as to be closed as it passes through the endoscope and is opened after passing through the endoscope when in the appropriate location. The brush is capable of being rotated and moved against the tissue so as to remove suspect tissue, and the brush is then closed and withdrawn from the endoscope. The tissue collected by the brush is then ultimately examined for potential cancerous or pre-cancerous conditions in accordance with well known cell examination techniques.

Focal sampling of questionable lesions of the nose and throat areas and of similar epithelia is provided using a stiff-bristled brush. By rubbing harder than normal cytological sampling and using a stiff device which penetrates epithelium, one can reach to the basement membrane without lacerating. As opposed to the prior art, use of the device allows cell sampling which can readily and consistently produce a trans-epithelial cytologic sample. That is, by utilizing the invention disclosed herein, cells can readily and consistently be obtained from all levels of the epithelium (basal, intermediate and superficial) of a suspect lesion, thus overcoming the limitation in the prior art of abnormal epithelial cells being inaccessible to cytology for a variety of reasons, including because they are covered by a keratin layer. The resulting cellular sample functionally approximates the cellular sample of a lacerating biopsy device but is obtained with the ease of a stiff brush sweeping and without discomfort to the patient. The subject invention therefore makes practical the routine testing of questionable lesions of the nasopharynx, hypopharynx, pharynx, trachea, larynx, and the upper esophagus, thus allowing early detection and treatment of cancer and pre-cancer of those areas.

While the preferred embodiment has been described with respect to a brush, the present invention generally describes a method and apparatus for obtaining transepithelial specimens of a body surface. The invention relates to a non-lacerational method and apparatus to obtain such a specimen. The reason one seeks to obtain a transepithelial sample is because suspect cells appear at the superficial layer of the epithelium originate at the basal layer within the tissue. With respect to the nasopharynx, hypopharynx, pharynx, trachea, larynx, and the upper esophagus, basal cells originate in the general area of the basement membrane separating the epithelial tissue from the tissue below the membrane known as the submucosa. In determining whether or not a patient has a precancerous or cancerous condition, it is important to reach down to the basement membrane and slightly therebelow because metastases may be suspected depending on the cellular architecture existing at just below or at the basement membrane through to the superficial layer.

The structure of the brush and bristles including the stiffness thereof as well as the shape of the bristle tips contribute to the effectiveness of the brushing or scrubbing action in retrieving cells from the transepithelial layers. The shape of the bristle tips is determined by the bristle cutting process. The bristle tips, preferably, have scraping edges. The tips of the brush and the brush itself may be considered as an assemblage of penetrating edges.

DETAILED DESCRIPTION

The prior art has used brushes with endoscopes to sample the examined area by moving the bristles of the brush across the suspect tissue area. Such brushes are similar to those described above which remove cells from the superficial layer, and the bristles do not penetrate below such layer because there is no direct force applied pushing tips of the bristles into the tissue being examined. Further, the prior art brushes merely rub against the surface and the brush area is very limited. The present retractable brush opens to a large size, the bristles thereof directly bear on said tissue transversely thereto and are urged further into said tissue by direct pressure. The brush is then rotated to sample a large area while concurrently reaching through the basement membrane to the basal cell layer.

Figure 1:
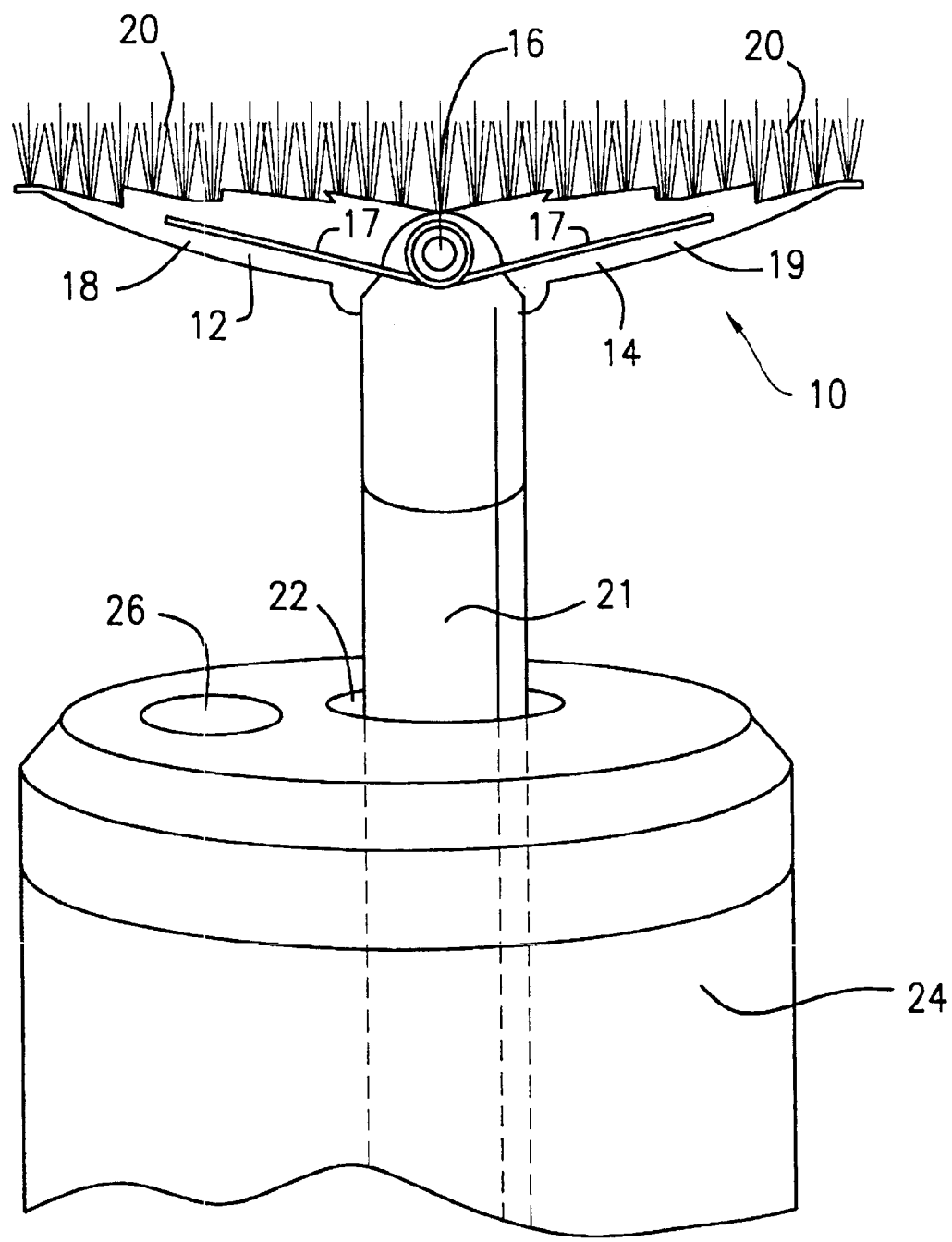
FIG. 1 is a partial perspective and sectional view illustrating the retractable brush in an open position after passing through the endoscope.

FIG. 1 is a partial perspective and sectional view of an embodiment of this invention comprising a brush 10 formed of two separate brush sections 12 and 14 hingedly connected together as at 16 and outwardly biased by a spring 17 connected to rigid backbones 18 and 19 to which are attached bristles 20. The bristles 20 could be of different structures as in order to be more adapted to the environment in which the brushes will be employed. A cylindrical rigid rod 21 passes through a channel 22 in an endoscope 24 having a viewing lens or window 26 shown at the distal end of the endoscope. Endoscopes are commonly provided with channels through the instrument, such as 22 through which medical instruments pass in order to perform certain medical procedures which are employed in conjunction with the observational aspects of the endoscope 24.

Figure 2:
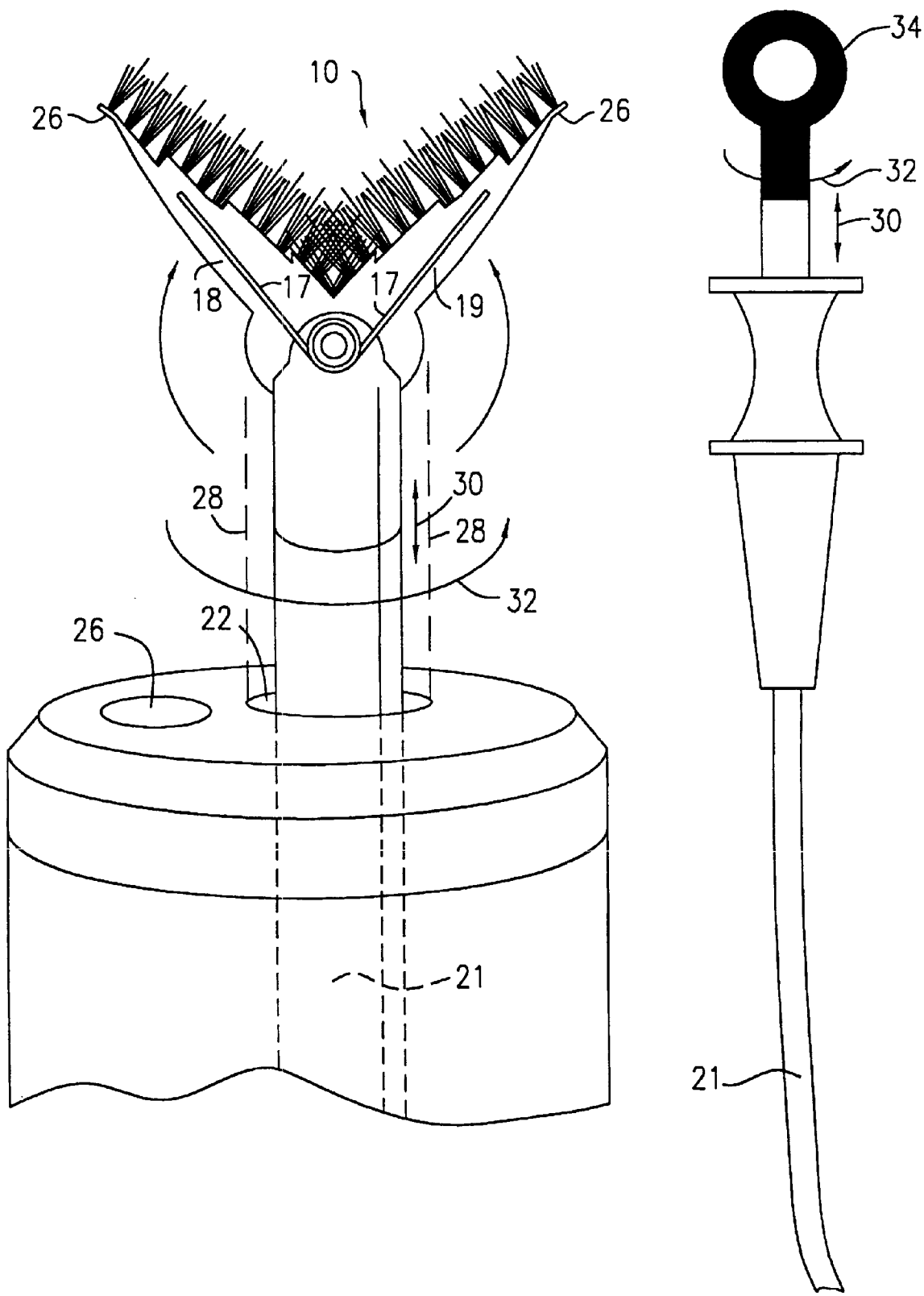
FIG. 2 is an exploded partial perspective and sectional view showing the handle manipulating the brush and illustrating the retractable brush folding together as it is drawn into the endoscope.

FIG. 2 is similar to FIG. 1 but shows the brush sections 18 and 19 being urged together against the pressure of spring 17 as the brush biopsy device of this invention is withdrawn in the endoscope as shown in dotted lines 28. Of course, it is understood that FIG. 2 also shows how the brush 10 opens when it is inserted through channel 22 and spring 17 forces the brush sections 12 and 14 to open fully. The area to be sampled is maximized by employing the retractable brush structure which can be narrow when closed to pass through the endoscope but open fully when in position to sample the suspected tissue.

The spring 17 applies a constant biasing force to the brush sections 12 and 14. In an equivalent structure, the force opening and closing the brush need not be continuous and need only be applied to open and close the brush sections 12 and 14 when they are in the proper position. The rigid rod 21 can be used for this purpose with conventional mechanical or hydraulic linkage. Before the brush is inserted in the patient, it is in a closed position with a distal front tip 26. The closed brush passes through channel. 22, and the brush sections 18 and 19 are opened after they pass through the endoscope into the examining area. The rigid rod 21 permits direct transverse pressure by the brush bristles against the tissue being examined and enables the brush to be rotated in order to remove cells from the epithelium tissue being examined, arrows 30 and 32 indicating the reciprocating and rotational movement at handle 34 which is transmitted to brush 10 by rod 21. Handle 34 is located at the proximal end. The rigid construction for backbone 17 and 18 assures a direct transfer of force from the user to the brush bristles 20 in order to effectively operate the brush. The retractable bristles in conjunction with the rigid rod allows a rotating or drilling action to be employed as desired.

As understood from the above, the bristles of the brush can penetrate through the basement membrane of the tissue under examination and reach into the basal cell layer so as to ensure that cells from all three layers are sampled. When the retractable brush closes either before or as it is withdrawn into the endoscope, the brush bristles also close retaining the sample cells. After the device is removed from the endoscope the brush again opens permitting the bristles to be wiped across a suitable carrier for later analysis of the cells deposited on the carrier.

The brush 10 is illustrative of a tissue removing structure, and other tissue removing structures may be employed. The size of the brush can be varied; the number and structure of bristles can be varied; the retractable brush structure can be varied so that more than one pair of bristles may be employed, all of which would be available to one of ordinary skill in the art seeking to utilize the present non-lacerational cell sampling technique in conjunction with an endoscope. In essence, the retractable front end brush allowing non-lacerational removal of tissue from a desired area by manipulation of a rigid rod passing through a channel in an endoscope provides enhanced benefits to patients who may have suspected lesions without having to perform lacerational biopsies on such patients.

Having described this invention with regard to specific embodiments, it is to be understood that the description is not meant as a limitation since further modifications and variations may be apparent or may suggest themselves to those skilled in the art. It is intended that the present application cover all such modifications and variations as fall within the scope of the appended claims.

What is claimed is:

1. An apparatus for use in conjunction with an endoscope, said endoscope comprising a channel extending the length of the endoscope; said endoscope being sized to fit into the nasopharynx, hypopharynx, pharynx, trachea, larynx, or the upper esophagus areas of a patient; said apparatus comprising a rod passing through said channel having a distal and a proximal end; a retractable non-lacerational tissue remover having closed and open positions, said tissue remover attached to the distal end of said rod, said tissue remover being in a closed position as said rod passes through said endoscope, and a force applied to said tissue remover to open said tissue remover after it passes through said channel, said tissue remover bearing transversely against the tissue being examined and being controlled by said rod to remove tissue from a tissue area being examined, said tissue remover comprising means to non-lacerationally remove cells from at least two contiguous tissue layers in said nasopharynx, hypopharynx, pharynx, trachea, larynx, or the upper esophagus areas of a patient; said retractable tissue remover being closed before being withdrawn from said endoscope, so as to retain the collected cells and remove them as the closed tissue remover is withdrawn from the endoscope.

2. An apparatus as set forth in claim 1, wherein said tissue remover comprises a retractable brush.

3. An apparatus as set forth in claim 2, wherein said retractable brush comprises a pair of bristle structures hingedly joined together by a biasing force biasing said pair of bristles open to bear transversely against the tissue being examined.

4. An apparatus as set forth in claim 1, wherein said rod is rigid, said retractable non-lacerational tissue remover being in a closed position to pass through said channel, said rod being manipulated to open said tissue remover after it passes through said channel in order to remove tissue.

5. An apparatus as set forth in claim 2, wherein said rod is rigid.

6. An apparatus as set forth in claim 5, wherein said retractable brush is opened after being withdrawn from said endoscope to allow collection of cells therefrom.

7. An apparatus as set forth in claim 1, wherein said channel is interior to said endoscope.

8. An apparatus as set forth in claim 3, wherein said bristle structure of each member of said pair of said bristle structures comprises substantially similar structure.

9. An apparatus as set forth in claim 3, further comprising a spring hingedly joining said bristle structures, said spring bearing said bristle structures to a full open position.

10. An apparatus for use in conjunction with an endoscope to examine tissue cells located within and below a keratinized layer, said endoscope comprising a channel extending the length of the endoscope; said endoscope being sized to fit in the nasopharynx, hypopharynx, pharynx, trachea, larynx, or the upper esophagus areas of a patient; said apparatus comprising a rod passing through said channel having a distal and a proximal end; a retractable non-lacerational tissue remover attached to the distal end of said rod, said tissue remover comprising a brushing apparatus which is movable to bear against the tissue being examined and being controlled by said rod to remove tissue from a tissue area being examined, said brushing apparatus comprising bristles which exert sufficient pressure to dislodge cells in and under said keratinized layer in said nasopharynx, hypopharynx, pharynx, trachea, larynx, or the upper esophagus areas of a patient.

11. An apparatus as set forth in claim 10, wherein said tissue cells exist in superficial, intermediate and basal layers, said bristles penetrating into at least said superficial and intermediate layers.

12. An apparatus as set forth in claim 10, wherein said bristles penetrate into said basal layer.

13. An apparatus as set forth in claim 10, wherein said keratinized layer comprises multiple layers of keratinized cells, said bristles penetrating said multiple layers.

* * * * *